US00PP23292P3

(12) United States Plant Patent
Marczynski

(10) Patent No.: US PP23,292 P3
(45) Date of Patent: Jan. 1, 2013

(54) *CLEMATIS* PLANT NAMED 'BEAUTIFUL BRIDE'

(50) Latin Name: ***Clematis* sp.**
Varietal Denomination: Beautiful Bride

(76) Inventor: Szczepan Witold Marczynski, Pruszkow (PL)

( * ) Notice: Subject to any disclaimer, the term of this patent is extended or adjusted under 35 U.S.C. 154(b) by 94 days.

(21) Appl. No.: 12/930,893

(22) Filed: Jan. 19, 2011

(65) Prior Publication Data

US 2012/0185979 P1 Jul. 19, 2012

(51) Int. Cl.
*A01H 5/00* (2006.01)

(52) U.S. Cl. ..... Plt./228

(58) Field of Classification Search ..... Plt./228
See application file for complete search history.

(56) References Cited

PUBLICATIONS

GTITM UPOVROM Citation for 'Beautiful Bride' as per PL PBR PWA0009; Jan. 15, 2010.*

* cited by examiner

*Primary Examiner* — Kent L Bell
(74) *Attorney, Agent, or Firm* — Jondle & Associates, P.C.

(57) ABSTRACT

A new and distinct variety of *clematis* plant named 'Beautiful Bride' particularly distinguished by its large, white, star-shaped flowers and long, pointed tepals, is disclosed.

2 Drawing Sheets

Genus and species: *Clematis* sp.
Variety denomination: 'Beautiful Bride'.

BACKGROUND OF THE NEW PLANT

The present invention relates to a new and distinct *clematis* variety designated 'Beautiful Bride' and botanically known as *Clematis* sp. This new *clematis* variety was discovered in Pruszków, Poland and originated from an open pollination between the female *clematis* plant 'Mrs. Cholmondeley' (unpatented) and unknown *clematis* pollen parents (unpatented). 'Beautiful Bride' was first asexually propagated via vegetative softwood cuttings. 'Beautiful Bride' was subsequently asexually propagated and underwent further testing in Pruszków, Poland. The present invention has been found to be stable and reproduce true to type through successive asexual propagations via softwood cuttings.

SUMMARY OF THE INVENTION

The following are the most outstanding and distinguishing characteristics of this new variety when grown under normal horticultural practices in Pruszków, Poland:

1. Large, white flowers;
2. Star-shaped flowers; and
3. Long, pointed tepals.

PLANT BREEDERS RIGHTS

Plant Breeders Rights have been applied for in Poland on Dec. 15, 2009. 'Beautiful Bride' has not been sold or made publicly available anywhere in the world more than one year prior to the filing date of this application.

DESCRIPTION OF THE PHOTOGRAPHS

This new *clematis* plant is illustrated by the accompanying photographs which show the overall plant habit, buds, and flowers. The colors shown are as true as can be reasonably obtained by conventional photographic procedures. The photographs are of plants that are 3 years old.

DESCRIPTION OF THE NEW VARIETY

Figure 1:
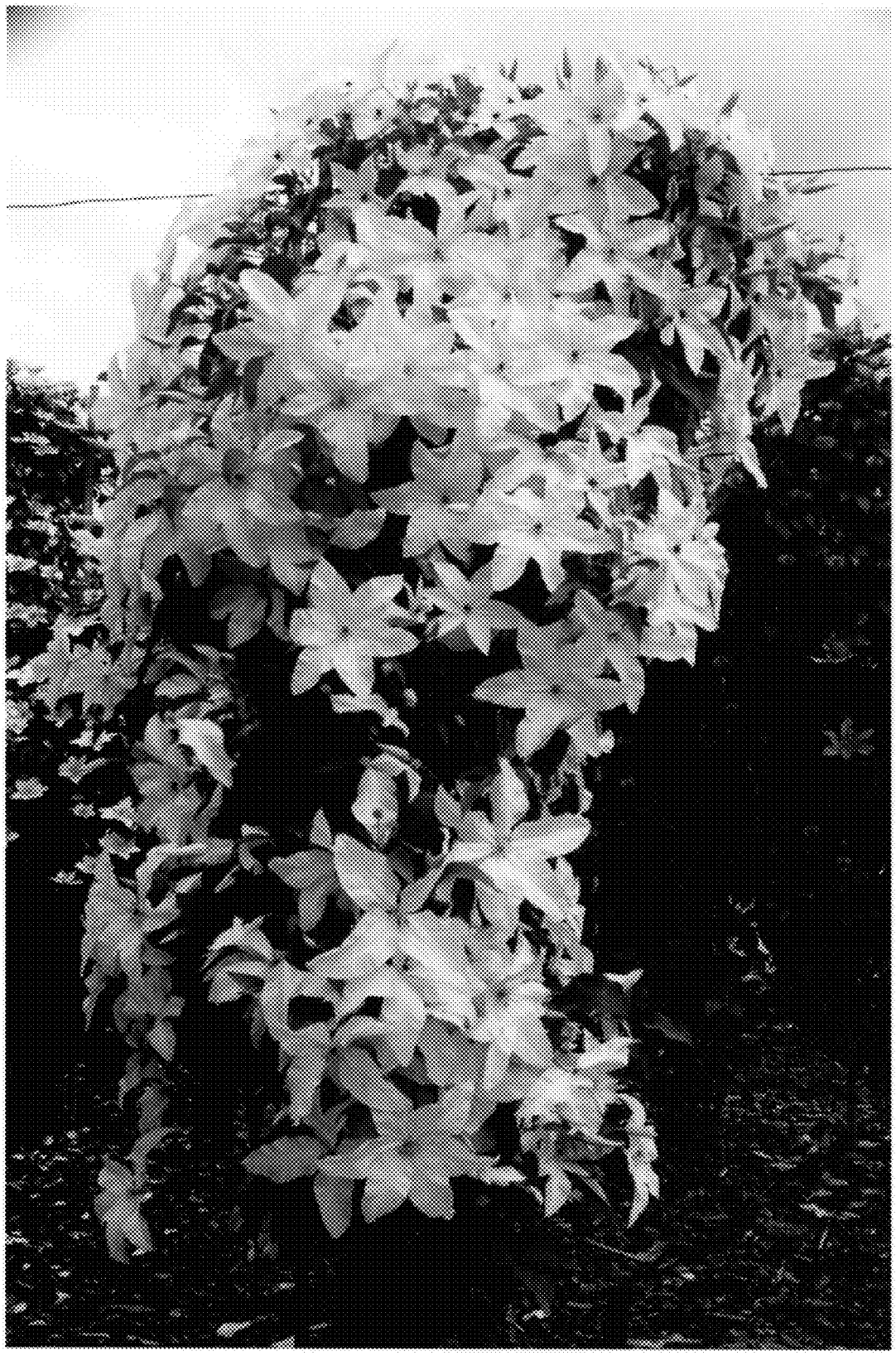
FIG. 1 shows the overall plant habit.
Figure 2:
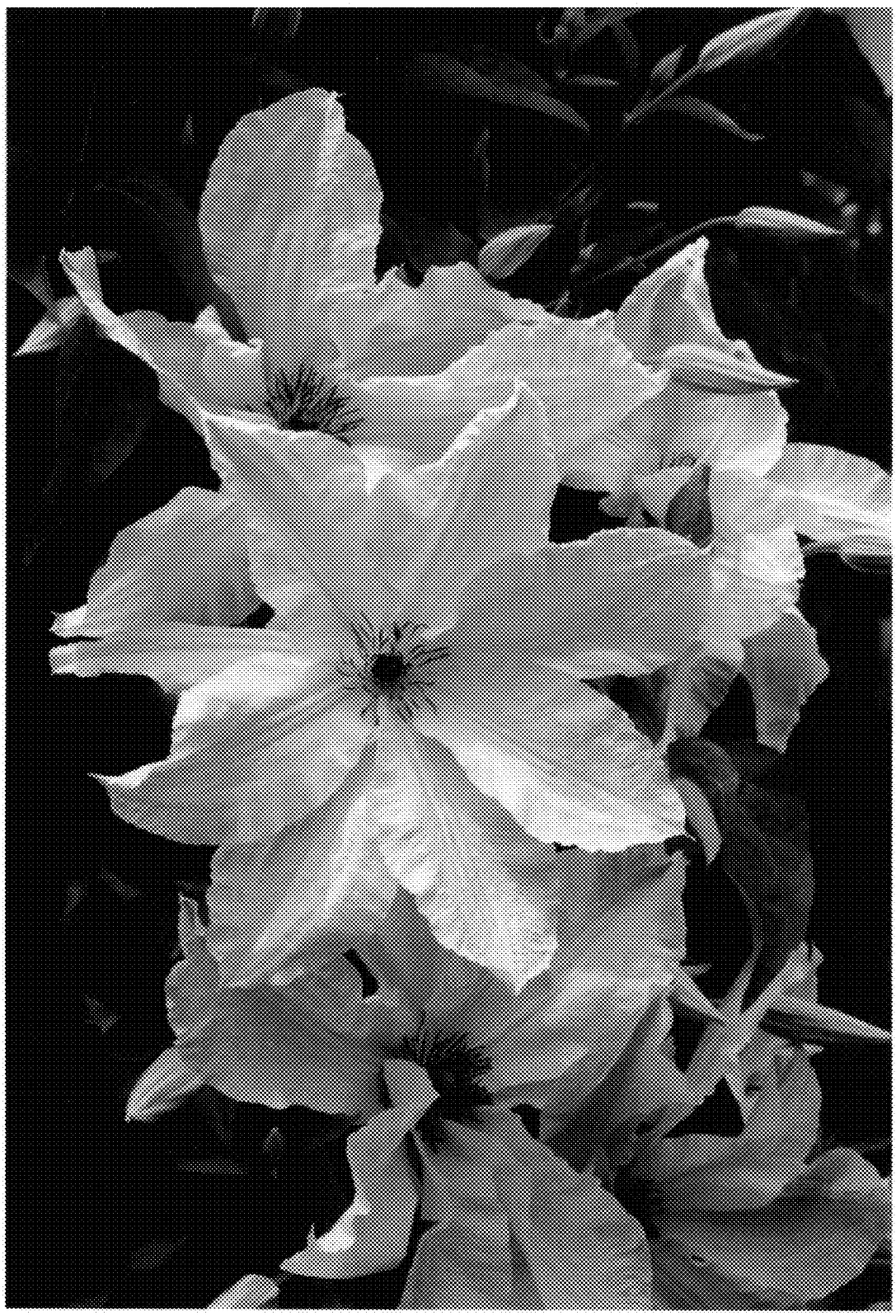
FIG. 2 shows a close up of the buds and flowers.

The following description of 'Beautiful Bride' is based on observations taken on three year old plants in Pruszków, Poland. This description is in accordance with UPOV terminology. Color designations, color descriptions, and other phenotypical descriptions may deviate from the stated values and descriptions depending upon variation in environmental, seasonal, climatic, and cultural conditions. 'Beautiful Bride' has not been observed under all possible environmental conditions. Color references are primarily to The R.H.S. Colour Chart of The Royal Horticultural Society of London (R.H.S.) (2001).

DETAILED BOTANICAL DESCRIPTION

Classification:
- *Family*.—Ranunculaceae.
- *Botanical*.—*Clematis* sp.
- *Common name*.—*Clematis*.
- *Variety name*.—'Beautiful Bride'.

Propagation:
- *Type*.—By stem, softwood cuttings.
- *Time to produce a rooted young plant, summer*.—12 weeks.
- *Root description*.—Bundle root system.
- *Rooting habit*.—Adventitious roots developing from cambial callus.

Plant description:
- *Form*.—Climber.
- *Plant habit*.—The leafstalks or petioles wrap around convenient supports and help the plant climb.

*Plant height.*—200.0 cm to 250.0 cm.
*Plant width.*—100.0 cm.

Branching:
*Lateral branch.*—Quantity: 7. Length: 20.0 cm to 30.0 cm. Diameter: 0.2 cm to 0.3 cm. Internode length: 4.0 cm to 8.0 cm. Texture: Many-ribbed, downy hairs on young shoots. Color: Immature: RHS 144B, early in season RHS 58A. Mature: RHS 166A.

Foliage description:
*Arrangement.*—Opposite.
*Type.*—Simple and ternate.
*Quantity of simple leaves per lateral branch.*—22.
*Quantity of ternate leaves per lateral branch.*—8.
*Length.*—Simple 15.0 cm to 17.0 cm, ternate 16.0 cm to 22.0 cm.
*Width.*—Simple 4.5 cm, ternate 15.0 cm to 18.0 cm.
*Shape.*—Immature leaf is lanceolate, mature leaf is pointed-ovate.
*Apex.*—Taper-pointed.
*Base.*—Narrowed.
*Margin.*—Entire; when immature, downy hairs are present.
*Texture.*—Upper surface: Smooth, matt, main vein is concave. Lower surface: Smooth, glossy, main vein is convex.
*Venation pattern.*—Net pattern.
*Venation color.*—RHS 144B; Pale, grey-green.
*Foliage color.*—Immature (both surfaces): RHS 143C. Mature (both surfaces): RHS 144B.
*Terminal leaflet.*—Length: 8.0 cm to 10.0 cm. Width: 2.5 cm to 4.5 cm. Shape: Pointed-ovate. Apex: Taper-pointed. Base: Narrowed. Margin: Entire; when immature, downy hairs are present. Texture: Upper surface: Smooth, matt, main vein is concave. Lower surface: Smooth, glossy, main vein is convex. Venation pattern: Net pattern. Foliage color: Immature (both surfaces): RHS 143C. Mature (both surfaces): RHS 144B.
*Lateral leaflets.*—Length: 8.0 cm to 10.0 cm. Width: 2.5 cm to 4.5 cm. Shape: Pointed-ovate. Apex: Taper-pointed. Base: Narrowed. Margin: Entire; when immature, downy hairs are present. Texture: Upper surface: Smooth, matte, main vein is concave. Lower surface: Smooth, glossy, main vein is convex. Venation pattern: Net pattern. Foliage color: Immature (both surfaces): RHS 143C. Mature (both surfaces): RHS 144B.
*Petiole.*—Length: 2.0 cm to 4.0 cm. Diameter: 0.1 cm to 0.2 cm. Color (both surfaces): RHS 59C. Texture: Has downy hairs.
*Petiolule.*—Length: 2.0 cm to 4.0 cm. Diameter: 0.1 cm to 0.2 cm. Color: In shade: RHS 144C. In sun: RHS 59C.

Flower description:
*Inflorescence type.*—Compound cymes.
*Flower arrangement and shape.*—Flat or flattish, star-shaped, upward- or outward-facing.
*Number of flowers.*—In cymes, 5 to 11; on the plant, over 50.
*Flower aspect.*—Upward- or outward-facing.
*Natural flowering season.*—Late May on previous year's growth, to August on current year's vines.
*Flower longevity on the plant.*—7 to 10 days.
*Fragrance.*—Absent.
*Flower buds.*—Length: 6.0 cm to 8.0 cm. Diameter: 1.5 cm to 2.0 cm. Shape: Long, pointed, downy. Color: RHS 145D.
*Flowers.*—Diameter: 18.0 cm to 28.0 cm. Depth (height): 1.0 cm to 4.0 cm.
*Tepals.*—Quantity and arrangement: 6 and overlapping. Length: 9.0 cm to 13.0 cm. Width: 4.5 cm to 6.0 cm. Shape: Narrow elliptic to broad lanceolate and ribby. Apex: Long-pointed. Base: Narrow elliptic to broad lanceolate. Margin: Ondulate. Texture: Upper surface: 3 ribs concave, surface slightly wrinkled. Lower surface: 3 ribs convex, surface slightly wrinkled. Color when opening: Upper surface: Close to RHS NN155C, white. Lower surface: RHS NN155D, white with RHS 155A bar in the middle. Color when fully open: Upper surface: RHS NN155C, white; sometimes with a very light bar of RHS 62D. Lower surface: RHS NN155D, white with RHS 155B bar in the middle.
*Peduncles.*—Length: 2.0 cm to 6.0 cm. Diameter: 0.3 cm to 0.4 cm. Texture: Downy hairs present. Color: RHS 144C, with RHS 64C.

Reproductive organs:
*Stamens.*—Quantity per flower: About 100.
*Filament length.*—1.0 cm to 1.5 cm.
*Filament color.*—RHS NN155D; Lemon-colored.
*Anther shape.*—Elongated.
*Anther length.*—0.5 cm.
*Anther color.*—RHS N187A; Connectives are purple; anthers are white.
*Pollen amount.*—Sparse.
*Pollen color.*—RHS NN155D; Grey-white.
*Pistils.*—Quantity per flower: 15 to 30. Length: 2.0 cm.
*Stigma color.*—RHS NN155C; Lemon-colored.
*Style length.*—1.0 cm.
*Style color.*—Lemon-colored. Base: RHS 157A. Upper side: RHS 157D.
*Ovary color.*—RHS 145B; Lemon-colored.

Seed production: Many seed/fruit, fruit-heads persistent.
*Amount.*—Varied, numerous.
*Diameter.*—0.6 cm to 0.9 cm.
*Color.*—RHS 166C.

Disease resistance: Typical of species.
Hardiness: Down to −35° C.

COMPARISON WITH PARENTAL AND COMMERCIAL VARIETIES

When 'Beautiful Bride' is compared with the female parent 'Mrs. Cholmondeley' (unpatented), 'Beautiful Bride' has white flowers, a flower diameter of 18.0 cm to 28.0 cm, and long-pointed tepals, while 'Mrs. Cholmondeley' has blue flowers, a flower diameter of 15.0 cm to 20.0 cm, and mucronate-tipped tepals.

When 'Beautiful Bride' is compared to the commercial variety 'Marie Boiselot' (unpatented), 'Beautiful Bride' has six star-shaped and narrow tepals and a flower diameter of 18.0 cm to 28.0 cm, while 'Marie Boiselot' has eight broad and blunt tepals and a flower diameter of 15.0 cm to 20.0 cm.

I claim:

1. A new and distinct variety of *Clematis* plant named 'Beautiful Bride' as described and shown herein.

* * * * *